(12) United States Patent
Bellani et al.

(10) Patent No.: US 6,433,177 B1
(45) Date of Patent: Aug. 13, 2002

(54) PROCESS FOR THE PREPARATION OF (S)-N-TERT-BUTYL-1,2,3,4-TETRAHYDROISOQUINOLINE-3-CARBOXAMIDE

(75) Inventors: Pietro Bellani; Aldo Banfi, both of Milan (IT)

(73) Assignee: Clariant LSM Italia S.P.A., Origgio (Varese) (IT)

( * ) Notice: Subject to any disclaimer, the term of this patent is extended or adjusted under 35 U.S.C. 154(b) by 0 days.

(21) Appl. No.: 09/478,657

(22) Filed: Jan. 6, 2000

(30) Foreign Application Priority Data

Nov. 25, 1999 (IT) .......................... MI99A2457

(51) Int. Cl.[7] .................. C07D 217/12; C07D 217/22; C07D 217/02; C07D 491/048
(52) U.S. Cl. .......................... 546/146; 546/140; 546/89
(58) Field of Search ................. 546/146, 140, 546/89

(56) References Cited

U.S. PATENT DOCUMENTS 5,587,481 A * 12/1996 Allen et al. ................. 546/146

FOREIGN PATENT DOCUMENTS

| EP | 0751128 | * | 1/1997 | ................. 546/146 |
| JP | 10291979 | | 11/1998 | |

* cited by examiner

Primary Examiner—Bernard Dentz
(74) Attorney, Agent, or Firm—Darby & Darby

(57) ABSTRACT

It is here described a new process for the synthesis of (S)-N-tertbutyl-1,2,3,4-tetrahydroisoquinoline-3-carboxamide wherein the N-carboxy anhydride of formula

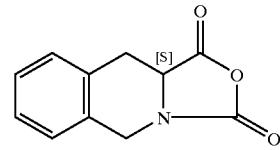

is treated with tert-butylamine in an organic inert solvent, preferably toluene, at a temperature of between −80 and −30° C.

18 Claims, No Drawings

PROCESS FOR THE PREPARATION OF (S)-N-TERT-BUTYL-1,2,3,4-TETRAHYDROISOQUINOLINE-3-CARBOXAMIDE

BACKGROUND OF THE INVENTION

The present invention relates to a new process for the preparation of (S)-N-tert-butyl-1,2,3,4-tetrahydroisoquinoline-3-carboxamide whose formula of structure is here below reported

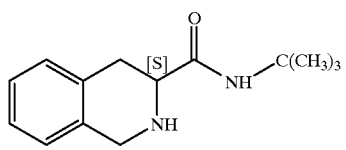

and which is a key intermediate for the preparation of compounds having elevated pharmacological activity, which can be used in particular in the treatment and in the prevention of infections caused by HIV. In the greatest part of said antiviral drugs the (S)-N-tert-butyl-1,2,3,4-tetrahydroisoquinoline-3-carboxamide is not used directly as such but, contrarily is previously hydrogenated to form the N-tert-butyl-decahydro-(4aS,8aS)isoquinolin-3(S)-carboxamide whose formula of structure is here below reported

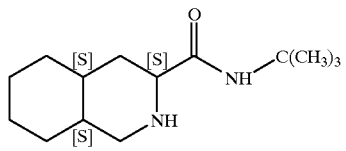

and by suitable substitutions at the isoquinoline nitrogen which will be obvious to any person skilled in the art is in turn converted into the pharmacologically active derivative.

In U.S. Pat. No. 5,196,438, herein incorporated as a reference, pharmacologically active compounds are disclosed whose formula of structure is here below reported

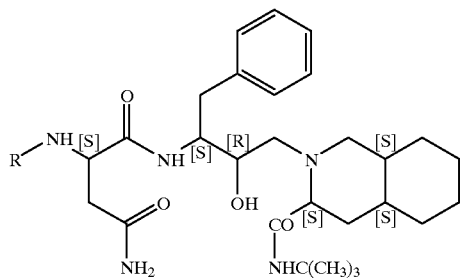

and in which the decahydroisoquinoline residue derived from the N-tert-butyl-decahydro-(4aS,8aS)-isoquinolin-3 (S)-carboxamide is immediately identifiable; among these, the derivative of most interest, and the structural formula of which is given below

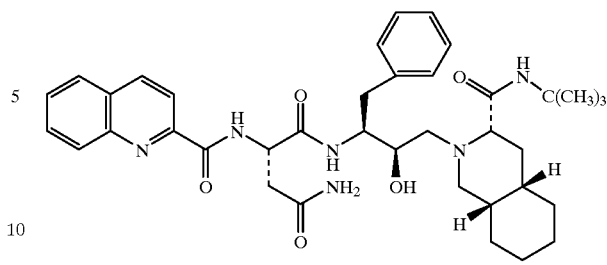

is known by the commercial name Saquinavir.

Another anti-viral drug of substantial importance, which also contains the decahydroisoquinoline residue present in Saquinavir, is Nelfinavir, the structural formula of which is likewise given below

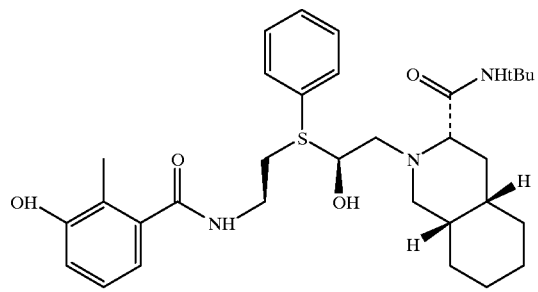

Both Nelfinavir and Saquinavir are normally used in the form of the corresponding water-soluble salts and, in particular, in the form of the mesylated salts.

In U.S. Pat. No. 5,587,481 it is described a process for the manufacture of the (S)-N-tert-butyl-1,2-3,4-tetrahydroisoquinoline-3-carboxamide wherein the (3S)-1,2,3,4-tetrahydroisoquinoline-3-carboxylic acid

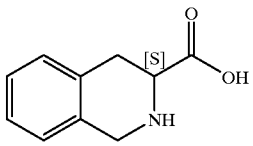

is reacted with phosgene in ethyl acetate to produce the corresponding N-carboxyanhydride (NCA), here below reported

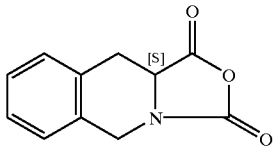

The NCA is then directly reacted with tert-butylamine and subsequently hydrogenated to give the N-tert-butyl-decahydro-(4aS,8aS)-isoquinolin-3(S)-carboxamide The process disclosed in U.S. Pat. No. 5,587,481 is however characterized by drawbacks which cannot be neglected as low yields and, in particular, the fact of using phosgene, which is a toxic and highly dangerous gas.

European Patent Application EP 751128 describes a similar synthesis process in which the conversion of the (3S)-1,2,3,4-tetrahydroisoquinoline-3-carboxylic acid into the corresponding NCA can be effected also with triphosgene. The advantages resulting from this process are clear because the use of triphosgene which, unlike phosgene, is not a toxic gas, permits complete safety of implementation with a consequent saving in operating costs and plant costs; triphosgene is also a solid compound which enables it to be used more accurately and therefore without the typical secondary reactions which may occur with the use of a gaseous reagent in excess.

Finally, the Italian patent application MI98A001478 filed on Jun. 26, 1998, describes an implemented process for the synthesis of the (S)-N-tert-butyl-1,2,3,4-tetrahydroisoquinoline-3-carboxamide characterized in that the (3S)-1,2,3,4-tetrahydroisoquinoline-3-carboxylic acid is reacted with triphosgene in dioxane making it possible to obtain particularly high global yields also on an industrial scale.

Both U.S. Pat. No. 5,587,481, EP-751128 and MI98A001478 present the common feature that the reaction between NCA and tert-butylamine is carried out at a starting temperature higher than −20° C.

SUMMARY OF THE INVENTION

It has now been surprisingly found and it is the object of the present invention, that by carrying out the reaction between tert-butylamine and the NCA at a starting temperature lower than −30° C., preferably lower than −50° C., the (S)-N-tert-butyl-1,2,3,4-tetrahydroisoquinoline-3-carboxamide is produced with a yield and a purity definitely higher than those obtainable by carrying out the reaction according to the previously described methods. In particular, as it will be appreciated by the following examples, the reaction carried out according to the present invention permits the obtainment of the (S)-N-tert-butyl-1,2,3,4-tetrahydroisoquinoline-3-carboxamide with yields of 15–20% higher than those obtainable by operating at a starting temperature higher than −20° C. Furthermore, the reaction between tert-butylamine and the NCA carried out according to the previously described methods produces a dimer by-product, whose formula is here below reported

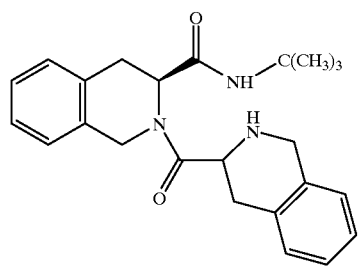

which is on the contrary produced in substantially reduced amounts if operating according to the method of the present invention.

DETAILED DESCRIPTION OF THE INVENTION

The reaction between NCA and tert-butylamine is carried out in an inert organic solvent, preferably toluene, THF, dioxane, methylene chloride, using from 1 to 10 moles of tert-butylamine, preferably from 3 to 5 moles, for each mole of NCA.

The NCA is generally suspended in 5–10 liters of solvent for 1 kg of NCA. The so-obtained suspension is then normally cooled to a temperature lower than −50° C., preferably at a temperature comprised between −80—50° C., more preferably at −75—−65° C. The tert-butylamine is then added maintaining the temperature below −50° C., preferably below −55° C.; the temperature is then raised until room temperature and maintained as such until completion of the reaction.

The method for the manufacture of the NCA is not limiting for the purposes of the present invention and can be carried out according to the several methods reported in literature; the preferred method is however that disclosed in MI98A001478 and wherein the (3S)-1,2,3,4-tetrahydroisoquinoline-3-carboxylic acid is reacted with triphosgene in dioxane at a starting concentration of 0.5–1.5 m/l with 0.3–1.2 equivalents of triphosgene and at temperatures between +20 and +85° C.

In the preferred embodiment of the invention, the NCA thus obtained is not isolated; on the contrary, the solvent of the previous reaction is distilled off and the raw NCA is then directly suspended in the reaction solvent, preferably in toluene; normally 3000–5000 liters of solvent, preferably 3500–4500, are used for 500 kg of (3S)-1,2,3,4-tetrahydroisoquinoline-3-carboxylic acid. The reaction mixture is then cooled to about −70° C. and the tert-butylamine is then added dropwise into the solution for a time period of 20–40 minutes, maintaining the temperature below −55° C.; the temperature is then raised to about −20° C. in 20–40 minutes and it is then raised to +15–+20° C. in 20–40 minutes. The temperature is then maintained as such for about 2 hours and water is added afterwards in order to quench the reaction.

The end product is then isolated in accordance with conventional techniques; preferably it is precipitated from acidic water by addition of a base, generally soda.

The (S)-N-tert-butyl-1,2-3,4-tetrahydroisoquinoline-3-carboxamide can then be hydrogenated to N-tert-butyl-decahydro-(4aS,8aS)-isoquinoline-3(S)-carboxamide in accordance with conventional techniques as those described in U.S. Pat. No. 5,256,783, U.S. Pat. No. 5,587,481, EP-751128 and MI98A001478, herein incorporated as a reference; the reaction is normally carried out in an organic polar solvent, preferably an alcohol, even more preferably isopropanol, in the presence of a reduction catalyst in heterogeneous phase, preferably rhodium supported on alumina.

Those and other aspects of the invention will become clear from the following examples which are to be regarded purely as non-limiting illustrations of the invention.

EXAMPLE 1

In the following table there are reported the results of experiments carried out in toluene on 5 g of isolated NCA (40 ml, KF=0,02%) with 3 equivalents of tert-butylamine. The reactions have been carried out maintaining the temperatures indicated in column B for the whole time indicated in column D; only the temperature of test 8 was maintained at −40° C. for the first hour and then raised to room temperature for the 3 following hours. The yields in solution were determined via HPLC.

| A Test | B Temperature (° C.) | C tBaNH₂ addition time (min) | D Total reaction time (ore) | E Average yield (%) | F Dimer (area %) |
|---|---|---|---|---|---|
| 1 | −7° C. | 5 | 3 | 94.5 | 2.46–2.47 |
| 2 | −7° C. | 60 | 3 | 94.5 | 2.26–2.21 |
| 3 | −7° C. | 5 | 4 | 89.2 | 2.29–2.42 |
| 4 | −7° C. | 60 | 4 | 91.0 | 2.31–2.33 |
| 5 | −7° C. | 5 | 6 | 92.7 | 2.46–2.47 |
| 6 | −7° C. | 60 | 6 | 94.0 | 2.45–2.46 |
| 7 | +13° C. | 5 | 3 | 92.7 | 2.82–3.59 |
| 8 | −40° C. 1 hour | 5 | 4 | 99.2 | 0.78–0.79 |

As it can be appreciated from the data listed in the table, by carrying out the reaction between tert-butylamine and NCA at a starting temperature lower than −20° C., it is possible to obtain substantially higher yields and a presence of dimer by-product considerably lower than by operating at a starting temperature higher than −20° C.

EXAMPLE 2

A triphosgene solution (83g, 0.28 mol) in dioxane (200 ml) has been added dropwise in 2 hours to a suspension of (3S)-1,2,3,4-tetrahydroisoquinoline-3-carboxylic acid (100 g, 0.564 mol) in dioxane (300 ml) under reflux. The mixture was then maintained under reflux (100° C.) under stirring for 30 minutes until complete dissolution. The solution has then been cooled to +75° C. −+85° C. in 10 and distilled off under vacuum in 2 hours and 30, maintaining the temperature at +40° C., until a dense but stirrable paste was obtained. The residue was then taken up twice with 100 ml of toluene and distilled off to give a stirrable paste. This was taken up again with 500 ml of toluene and cooled to −50° C.; the t-butylamine (180 ml, 1.709 mols) was then added dropwise in 30 minutes under stirring and in an inert atmosphere.

The temperature was then let to increase until +15° C. in 1 hour, the temperature was maintained at that temperature for 2 hours and 700 ml of water were then added. The organic phase was then extracted with water (800 ml) and 30% HCl at pH=1, the product was precipitated from the aqueous layer by addition of 30% NaOH, filtered, washed with water and cried under vacuum. 112.4 grams of product were obtained.

| | |
|---|---|
| Titer = | 99.11% |
| Purity HPL (A%) = | 99.32% |
| Dimer (HPLC, A%) = | 0.36% |
| Enantiomeric purity (A%) = | 98.9% |
| K.F. = | 0.21% |
| NaCl = | 0.24% |
| Yield = | 85.03% |

Comparative Examples

The reaction of example 2 was repeated by changing the starting 20 temperature and the time of t-butylamine dropwise addition only; the results are reported in the table.

| Test | Starting reaction temperature | Dropwise addition time | Yield (%) | Dimer (area %) | Titer (%) | Purity (%) |
|---|---|---|---|---|---|---|
| 2 | −40—50° C. | 20' | 85 | 0.36 | 99.1 | 99.3 |
| 2a | +10—+15° C. | 90' | 71 | 3.8 | 98.6 | 96 |
| 2b | −5—10° C. | 120' | 73 | 3.1 | 98.1 | 96.6 |
| 2c* | −5—10° C. | 120' | 73 | 1.3 | 99.8 | 98.6 |

*in test 2c t-butylamine was 1:1 diluted with toluene.

EXAMPLE 3

A solution of triphosgene (400 kg) dissolved in dioxane (1000 l) is added dropwise, with agitation, over a period of 2 hours to a mixture of (3S)-1,2,3,4-tetrahydroisoquinoline-3-carboxylic acid (500 kg) in dioxane (1500 l) heated to reflux. After one hour at that temperature, the whole is cooled to +40° C. and distilled to leave a residue. The residue is taken up twice in toluene (300 l) and distilled off to leave a residue which is again taken up in toluene (3500 l).

The so-obtained suspension is then cooled to −70° C. and a solution of tert-butylamine (900 l) is added in about 30 minutes, maintaining the temperature below −55° C. The temperature is then raised to about −20° C. in 30 minutes, and is raised to +15 to +20° C. in 30 further minutes; it is then maintained as such for 2 other hours.

The reaction is then quenched by adding demineralized water (3500 l); the organic phase is then extracted with water (3000 l) and 30% HCl (345 l), diluted with 2400 liters of water, treated with carbon, filtered and made basic with 30% soda until pH 11. The solid thus obtained is then filtered, washed with water and dried to give 524.4 kg of (S)-N-tert-butyl-1,2,3,4-tetrahydroisoquinoline-3-carboxamide (yield 80%; dimer 1–2%) as a white crystalline powder; purity>97% (HPLC), titer>98%.

The so obtained (S)-N-tert-butyl-1,2,3,4,-tetrahydroisoquinoline-3-carboxamide is then dissolved in about 1800 liters of isopropanol and subsequently hydrogenated at 45 bar on Rh/Al₂O₃ (5%, 8 kg) for 3–4 hours at a temperature of +70° C.; the catalyst is then filtered and washed with isopropanol. The solvent is evaporated and the raw material is taken up with heptane; the solvent is evaporated and the raw material is again taken up with heptane (120 l) and cooled to +0−+5° C. for 1 hour.

The final product is then obtained after filtration and washing with heptane, as a white crystalline powder (mp. 113 to 115° C.), with a yield of 88%.

The final product is then obtained after filtration and washing with heptane, as a white crystalline powder (mp. 113 to 115° C.), with a yield of 88%.

What is claimed is:

1. A process for the production of (S)-N-tert-butyl-1,2,3, 4-tetrahydroisoquinoline-3-carboxamide, comprising:

a) reacting (3S)-1,2,3,4-tetrahydroisoquinoline-3-carboxylic acid with triphosgene in dioxane to form an N-carboxyanhydride of the following formula

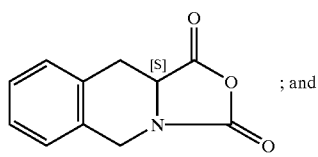
; and b) mixing the N-carboxyanhydride with tert-butylamine in toluene at an initial temperature lower than −50° C., and thereafter raising the temperature of the resulting mixture to produce the (S)-N-tert-butyl-1,2,3,4-tetrahydroisoquinoline-3-carboxamide.

2. The process of claim 1, wherein the (3S)-1,2,3,4-tetrahydroisoquinoline-3-carboxylic acid and triphosgene are reacted in step a) at a temperature between +20° C. and +105° C.

3. The process of claim 2, wherein the (3S)-1,2,3,4-tetrahydroisoquinoline-3-carboxylic acid and triphosgene are reacted in step a) under reflux.

4. The process of claim 1, wherein the (3S)-1,2,3,4-tetrahydroisoquinoline-3-carboxylic acid is reacted in step a) at an initial concentration of 0.5 to 1.5 m/l.

5. The process of claim 1, wherein the (3S)-1,2,3,4-tetrahydroisoquinoline-3-carboxylic acid is reacted with from with 0.3 to 1.2 equivalents of triphosgene in step a).

6. The process of claim 1, wherein the N-carboxyanhydride is suspended in 3000 to 5000 liters of solvent per 500 kg of the (3S)-1,2,3,4-tetrahydroisoquinoline-3-carboxylic acid in step a).

7. The process of claim 6, wherein the N-carboxyanhydride is suspended in 3500 to 4500 liters of solvent per 500 kg of the (3S)-1,2,3,4-tetrahydroisoquinoline-3-carboxylic acid in step a).

8. The process of claim 1, wherein the N-carboxyanhydride and tert-butylamine are initially mixed in Step b) at a temperature between −80° C. and −50° C.

9. The process of claim 8, wherein the N-carboxyanhydride and tert-butylamine are initially mixed in Step b) at a temperature between −75° C. and −65° C.

10. The process of claim 1, wherein the N-carboxyanhydride is reacted in step b) with from 1 to 10 equivalents of the tert-butylamine.

11. The process of claim 10, wherein the N-carboxyanhydride is reacted in step b) with from 3 to 5 equivalents of the tert-butylamine.

12. The process of claim 1 wherein the reaction in step b) is carried out in 5–10 liters of the toluene per kg of the N-carboxyanhydride.

13. A process for the production of (S)-N-tert-butyl-1,2,3,4-tetrahydroisoquinoline-3-carboxamide, comprising:

a) reacting (3S)-1,2,3,4-tetrahydroisoquinoline-3-carboxylic acid at an initial concentration of 0.5 to 1.5 m/l. with from 0.3 to 1.2 equivalents of triphosgene, in dioxane at a temperature between +20° C. and +105° C., to form an N-carboxyanhydride of the following formula

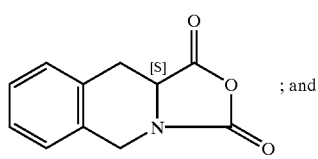
; and b) mixing the N-carboxyanhydride with tert-butylamine in toluene at an initial temperature lower than −50° C., with stirring, and thereafter raising the temperature of the resulting mixture to produce the (S)-N-tert-butyl-1,2,3,4-tetrahydroisoquinoline-3-carboxamide.

14. A process for the production of (S)-N-tert-butyl-1,2,3,4-tetrahydroisoquinoline-3-carboxamide, comprising:

a) reacting

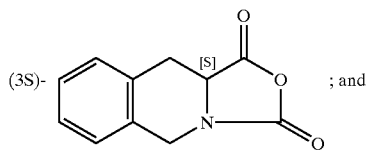
; and 1,2,3,4-tetrahydroisoquinoline-3-carboxylic acid with triphosgene in dioxane to form an N-carboxyanhydride of the following formula b) mixing the N-carboxyanhydride with from 1 to 10 equivalents of tert-butylamine in 5–10 liters of toluene per kg. of the N-carboxyanhydride, with stirring, at an initial temperature lower than −50° C., and thereafter raising the temperature of the resulting mixture to produce the (S)-N-tert-butyl-1,2,3,4-tetrahydroisoquinoline-3-carboxamide.

15. A process for the production of (S)-N-tert-butyl-1,2,3,4-tetrahydroisoquinoline-3-carboxamide, comprising:

a) reacting (3S)-1,2,3,4-tetrahydroisoquinoline-3-carboxylic acid at an initial concentration of 0.5 to 1.5 m/l. with from 0.3 to 1.2 equivalents of triphosgene, in dioxane at a temperature between +20° C. and +105° C., to form an N-carboxyanhydride of the following formula

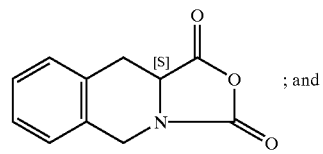
; and b) mixing the N-carboxyanhydride with from 1 to 10 equivalents of tert-butylamine in 5–10 liters of toluene per kg. of the N-carboxyanhydride, with stirring, at an initial temperature lower than −50° C., and thereafter raising the temperature of the resulting mixture to produce the (S)-N-tert-butyl-1,2,3,4-tetrahydroisoquinoline-3-carboxamide.

16. The process of claim 1, wherein (a) a solution of the N-carboxyanhydride in toluene is cooled to −75° to −65° C., (b) tert-butylamine is added to the solution dropwise for a period of from 20 to 40 minutes while maintaining the temperature of the reaction mixture below −55° C., (c) the temperature of the reaction mixture is then raised to about −20° C. in 20 to 40 minutes, (d) the temperature of the reaction mixture is then raised to +15 to +20° C. in 20 to 40 minutes and (e) the temperature of the reaction mixture is maintained constant until the reaction is completed.

17. The process of claim 1, wherein the (S)-N-tert-butyl-1,2,3,4-tetrahydroisoquinoline-3-carboxyamide is converted to N-tertbutyl-decahydro-(4aS,8aS)-isoquinoline-3(S)-carboxarmide by catalytic hydrogenation.

18. The process of claim 17, wherein the catalytic hydrogenation is carried out in isopropanol in the presence of rhodium supported on alumina.

* * * * *